United States Patent [19]

Gill et al.

[11] Patent Number: 4,931,553
[45] Date of Patent: Jun. 5, 1990

[54] PLATINUM-POLYMER COMPLEXES AND THEIR USE AS ANTITUMOR AGENTS

[76] Inventors: Devinder S. Gill, 11,800 Baltimore Ave., Beltsville, Md. 20705; Peter J. Andrulis, Jr., 7315 Wisconsin Ave., Bethesda, Md. 20814

[21] Appl. No.: 192,451

[22] Filed: May 11, 1988

[51] Int. Cl.$^5$ ...................... C07F 15/00; A61K 31/28
[52] U.S. Cl. .................... 536/121; 514/492; 514/908; 424/78; 556/137
[58] Field of Search ............ 536/121; 514/492, 908; 424/78; 556/137

[56] References Cited

U.S. PATENT DOCUMENTS

| | | | |
|---|---|---|---|
| 4,137,248 | 1/1979 | Gale et al. | 514/908 |
| 4,151,185 | 4/1979 | Allcock et al. | 525/340 |
| 4,169,846 | 10/1979 | Kidani et al. | 556/137 |
| 4,200,583 | 4/1980 | Kidani et al. | 536/55 |
| 4,283,342 | 8/1981 | Yolles | 536/6.4 |
| 4,551,524 | 11/1985 | Kidani et al. | 556/136 |
| 4,560,781 | 12/1985 | Totani et al. | 514/492 |
| 4,565,884 | 1/1986 | Andrulis, Jr. | 514/492 |
| 4,584,392 | 4/1986 | Smith et al. | 536/121 |
| 4,659,849 | 4/1987 | Drobník et al. | 556/137 |
| 4,673,754 | 6/1987 | Smith et al. | 536/121 |
| 4,680,308 | 7/1987 | Schwartz et al. | 514/492 |
| 4,720,504 | 1/1988 | Andrulis, Jr. | 514/492 |
| 4,767,874 | 8/1988 | Shima et al. | 556/137 |
| 4,793,986 | 12/1988 | Serino et al. | 556/137 |

OTHER PUBLICATIONS

Rochon et al., "Antitumor Evaluation of Some New Platinum Compounds", J. Clin. Hematol. & Oncol., 12 (1982), pp. 39-43.

Abstract, Andrulis, Jr. et al., "New Analogs of 4-carboxyphthalato(1,2-diaminocyclohexane)-Platinum (DACH-PT)" in Platinum Coordination Complexes in Cancer Chemotherapy (1983).

Durant, J. R., "Cisplatin: A Clinical Overview", in Cisplatin: Current Status and New Developments, Academic Press, NY, pp. 317-320 (1980).

*Primary Examiner*—Ronald W. Griffin
*Attorney, Agent, or Firm*—Millen, White & Zelano

[57] ABSTRACT

Platinum(amine) complexes, when covalently linked to a water-soluble, biodegradable or biostable polymer, exhibit high antitumor activity at low dosages of platinum against L1210 and solid tumors. The complexes are platinum square planar complexes and octahedral structures of the formulae

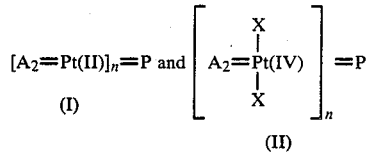

wherein $A_2$ represents either 2 ammonia ligands, 2 monodentate amine ligands or a single bidentate amine ligand; P is either a biodegradable or a biostable but biocompatible polymer having pendent anionic groups which form covalent linkages with Pt; o is a positive integer and X is an anionic ligand.

26 Claims, No Drawings

PLATINUM-POLYMER COMPLEXES AND THEIR USE AS ANTITUMOR AGENTS

BACKGROUND OF THE INVENTION

This invention relates to novel platinum-polymer conjugates, to pharmaceutical compositions comprising them, and to their use as antitumor agents in humans and animals.

It is known that cisplatin, i.e., cis-[Pt(NH$_3$)$_2$Cl$_2$] is effective against several types of animal tumors and has been used successfully in treating certain types of malignancies in humans. A number of other platinum complexes have been tested for antitumor activity, e.g., increased life span for mice having implanted tumors such as L-1210 lymphoid leukemia.

An oligomeric, platinum complex is disclosed in Yolles U.S. Pat. No. 4,283,342. These complexes contain bridging halogen ligands as well as a number of platinum ions in both therapeutic and non-therapeutic forms in the complex. Three bis-platinum complexes were reported by Rochon et al., *J. Clin. Hematology & Oncology*, 12, 39–43 (May, 1982). Two of those showed no activity against L-1210 lymphoid leukemia, while a third showed a low level of activity but also showed significant toxicity.

Andrulis and Schwartz, U.S. Pat. No. 4,680,308, claims 1,2-diaminocyclohexane complexes having substantial stability in water solutions.

Andrulis and Schwartz, U.S. Pat. No. 4,565,884, claims diamino bis-platinum complex having water solubility, antitumor activity and low toxicity. U.S. application Ser. No. 819,967, filed Jan. 21, 1986, now U.S. Pat. No. 4,720,504, claims the use thereof as antitumor agents.

Gale et al., U.S. Pat. No. 4,137,248, and Kidani et al., U.S. Pat. No. 4,169,846, disclose monomeric complexes of [1,2-diaminocyclohexane]Pt(II). Kidani et al., U.S. Pat. No. 4,200,583, discloses platinum(II) complexes of 1,2-diamino-cyclohexane and one or two sugar acid (Dglucuronic acid) moieties. The disclosures of the foregoing patents are incorporated herein by reference.

For Additional Relevant Literature see:
(a) J. Drobnik et al., U.S. Pat. No. 4,659,849, issued Apr. 21, 1987, "Macromolecular Coordination Compound Containing Platinum with Antitumor Activity in Rodents";
(b) C. E. Carraher et al., J. Polym. Sci. Tech. (Plenum), Vol. 25, 133 (1984); and
(c) H. R. Alcock et al., U.S. Pat. No. 4,151,185 (1979), "Complex or Salt of a Pt(II) Compound and a Nitrogen-Containing Polymer.

A need exists for platinum complexes with lower toxicity and/or which transport higher amounts of Pt to the tumor site, thereby enhancing antitumor activity.

OBJECTS OF THE INVENTION

An object of this invention is to provide novel platinum complexes having useful pharmaceutical activity.

Another object of the present invention is to provide novel platinum antitumor agents with enhanced antitumor activity at low platinum dosages.

Another object of the invention is to provide novel platinum delivery systems.

Another object is to provide a novel drug-delivery system for active platinum drugs by covalently linking them to pendant groups of the polymers, the polymers serving as ligands for complex formation and as carriers for enhanced solubility, sustained release, and preferential target-accessibility.

Still another object is to provide therapeutic platinum in a form which is advantageous for oral administration.

A still further object is to provide a method for reducing the amount of Pt in the form of a platinum amine complex having antitumor activity which must be administered to a human being or other animal to achieve an antitumor effective response and/or reducing the toxic side effects associated with the administration of an antitumor effective amount thereof.

A further object of this invention is to provide a method of tumor therapy which avoids disadvantages in prior art methods.

Other objects will be apparent to those skilled in the art to which this invention pertains.

SUMMARY OF THE INVENTION

In one composition aspect, this invention relates to platinum complexes of the formula

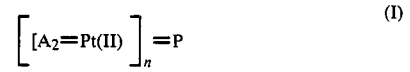

or

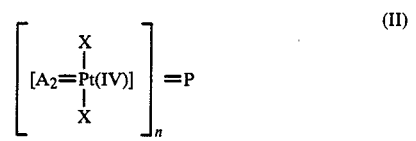

wherein each A independently represents a monodentate amine ligand or NH$_3$ or A$_2$ represents a single bidentate amine ligand, n is a positive integer; P is a divalent ligand of a physiologically acceptable polymer bearing at least 2×n pendant anionic groups, pairs of which form two covalent linkages with the A$_2$Pt(II) or A$_2$Pt(IV)X$_2$ groups; and X is an anionic ligand.

In another composition aspect, this invention relates to pharmaceutical compositions comprising an antitumor effective amount per unit dosage of a platinum complex of this invention in admixture with a pharmaceutically acceptable carrier.

In a method aspect, this invention relates to a method of treating a patient with a tumor which is susceptible to platinum therapy, which comprises administering to the patient an antitumor effective amount of a platinum complex of this invention.

In another method aspect, this invention relates to a method of solubilizing an at most sparingly soluble (<1 mg/ml) platinum-amine complexes, such as DACH-PtCl$_2$(II) or DACH-Pt(OH$_2$)Cl$_2$(IV), which comprises forming a polymer complex thereof with a water-soluble polymer having a plurality of acidic groups pendant from one or more polymer units of the polymer backbone. In a preferred embodiment, the production and isolation of the polymer complex is conducted at or below ambient temperature.

DETAILED DISCUSSION

The platinum of the polymeric platinum-amine complexes of this invention and of the platinum-amine complexes employed to produce them can be divalent or tetravalent.

Pt(IV) complexes are conveniently synthesized by oxidation of Pt(II) complexes, e.g., by reaction with hydrogen peroxide, normally at about 20°–80° C. It will be appreciated that, where the platinum ion is not a Pt(II) ion, e.g., Pt(IV) ion, an additional counterion will be required to balance the charge. This counterion will generally be selected from halide, hydroxide, nitrate, azide, other pseudohalides or other organic or inorganic anions. Oxidation of Pt(II) to Pt(IV) is described in, e.g., Cotton et al, "Advanced Inorganic Chemistry", p. 854 (John Wiley, 1962).

The ligand "A" can be $-NH_3$ or a monoamine group, i.e., $A_2$ can be two monodentate amine ligands, or it can be a diamine group, i.e., $A_2$ can be a single didentate amine ligand. The structure of the amine ligand A of the Pt-polymer complex is not critical, provided it does not impart excessive toxicity to the Pt-polymer complex in the amount administered. Examples of such amines are those of the formula $NR_1R_2R_3$ wherein $R_1$, $R_2$ and $R_3$ each independently is H, $C_{1-20}$ alkyl, $C_{320}$ carbocyclic or heterocyclic aryl, aralkyl or alkaryl or two of $R_1$, $R_2$ and $R_3$ together form one or more $C_{1-30}$ alkylene, $C_{3-20}$ carbocyclic or heterocyclic cycloalkylene, arylene, aralkylene or alkarylene groups. As stated above, the substituents on the amine groups coordinated to the platinum ion, $R_1$–$R_3$, can each independently be hydrogen atoms, $C_{1-20}$ alkyl, $C_3$–$C_{20}$ carbocyclic or heterocyclic groups, or pairs of substituents on the same or different amine nitrogen(s) can form one or more chains or rings, e.g., $C_{1-30}$ alkylene, $C_{3-20}$ carbocyclic or heterocyclic, cycloalkylene, arylene, aralkylene or alkarylene rings. The amine groups coordinated to the platinum ion need not be the same, i.e., different amine ligands with their attached to platinum atoms may be complexed to pendant groups of the polymers to provide synergism and to overcome cross-resisting; e.g., diamine Pt and DACH Pt may be complexed to a polymer chain to overcome cross-resistance. Examples of suitable amine coordinate groups include, e.g., ammonia, lower alkylamines, dialkylamines and trialkylamines, including straight-chain and branch-chain amines, e.g., methylamine, dimethylamine, triethylamine, dimethyl-isopropylamine, cyclic amines, e.g., pyrrolidine, N-methyl-pyrrolidine, piperidine, and the like; and diamines, e.g., ethylenediamine, 1,2,diaminocyclopentane and, preferably, 1,2-diaminocyclohexane (DACH) and especially trans-DACH. Also suitable are bidentate diamines having one amine function attached directly to an alicyclic ring, while the other is in the form of an aminomethyl substituent on the ring, e.g., 1-amino-2-aminomethylcyclohexane. This permits variation in the size of the chelate ring of bidentate amine substituents. The amine coordinating group(s) can be chiral, and the invention includes complexes made with mixtures of diastereomers, racemic mixtures and/or pure enantiomers of such chiral amines.

The polymer ligand P can be any physiologically acceptable acidic polymer which will form a covalent linkage with the platinum-amine complex. The term "physiologically acceptable" means that at a pharmaceutically effective dose the polymer is either biodegradable into acceptably assimilable or excretable fragments or it is biologically inert but excretable. The pendant anionic groups are preferably carboxylic acid groups. However, other acidic anionic groups, e.g., sulfato, phosphato, halides, pseudohalides, etc., are also operable. Because each platinum-amine complex forms with two of the pendant anionic groups, the starting polymer will contain at least twice the number of anionic groups as the platinum-amine complexes which are present in the complex of Formula I and II which embraces that polymer, i.e., the starting polymer will possess from $2 \times n$ to about $100 \times n$ or more. The polymer can have one or more such anionic groups as part of each polymeric structural unit, as in the case of the polyacrylic and polymethacrylic acids, or there can be one or more such anionic groups on only a portion, e.g., from about 10 to 90%, preferably about 40 to 60%, of the polymeric units, as in the case of partially oxidized polysaccharides. The pendant anionic group can be attached directly to the polymeric backbone or separated therefrom by a bridging divalent group, e.g., methylene, ethylene. The polymer can be a homopolymer, a copolymer or terpolymer.

Preferred biostable homopolymers are those having a weight average molecular weight ($\overline{M}_w$) from about 10,000 to about 50,000, preferably about 30,000 to 40,000, and most preferably about 20,000 to 30,000; especially those containing only C, H and O atoms (except for those present in a cation forming a salt therewith), e.g., hydrolyzed poly(maleic anhydride), poly(acrylic acid), poly(methacrylic acid), poly(ethacrylic acid), poly(salicyclic acid), hydrolyzed poly(maleic anhydride), etc.

Among copolymers, the following are especially preferred for complex formation with platinum: hydrolyzed poly(maleic anhydride-CO-divinylether), pyran copolymer; poly(maleic anhydride-CO-1,3-dimethyldioxepin); poly(maleic anhydride-CO-ethylene); poly(maleic anhydride-CO-allyl urea); poly(maleic anhydride-CO-cyclohexyl-1,3-dioxepin); poly(maleic anhydride-COstyrene); poly(maleic anhydride-CO-4-methyl-2-pentanone); poly(maleic anhydride-CO-acrylic acid); poly(maleic anhydride-CO-methacrylic acid); poly(maleic anhydride-CO-ethacrylic acid); poly(maleic anhydride-CO-allyl phenol); poly(maleic anhydride-CO-allyl-succinic anhydride); poly(maleic anhydride-CO-isobutenyl succinic anhydride); poly(maleic anhydride-CO-salicylic acid); poly(acrylic acid-CO-salicylic acid); and poly(methacrylic acid-CO-salicylic acid). The structures of some of these are set forth hereinbelow.

Preferred biodegradable polymers are those having a molecular weight ($\overline{M}_w$) of from 5,000 to 200,000, preferably from 50,000 to 180,000, especially those containing only C, H and O atoms (except for those present in a cation forming a salt therewith), including partially and fully oxidized oligosaccharides and polysaccharides, e.g., carboxyamylose, carboxyamylopectin, carboxymannan, carboxypullulan, carboxydextrans, carboxydextran sulfate, carboxycellulose, oxidized carboxymethylcellulose, oxidized carboxyethylcellulose, carboxypolygalacturonic acid, carboxyalginic acid, etc.

Illustrative structural formulae of such carboxysaccharide polymers are given on page 14.

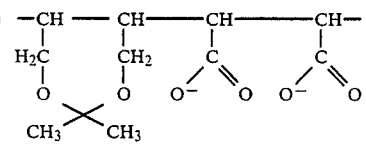

POLY(MALEIC ANHYDRIDE-
CO-1,3-DIMETHYLDIOXEPIN)
(MA-DD)

-continued

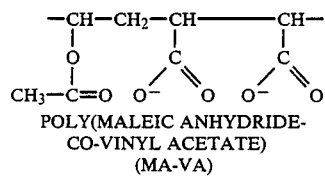

POLY(MALEIC ANHYDRIDE-
CO-VINYL ACETATE)
(MA-VA)

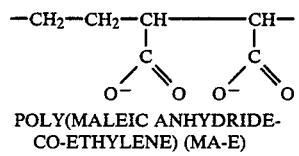

POLY(MALEIC ANHYDRIDE-
CO-ETHYLENE) (MA-E)

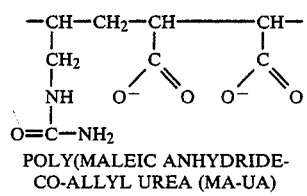

POLY(MALEIC ANHYDRIDE-
CO-ALLYL UREA (MA-UA)

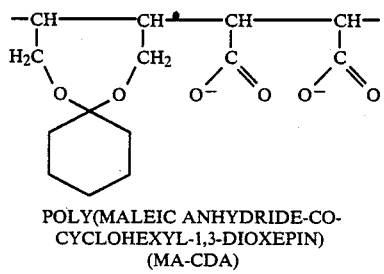

POLY(MALEIC ANHYDRIDE-CO-
CYCLOHEXYL-1,3-DIOXEPIN)
(MA-CDA)

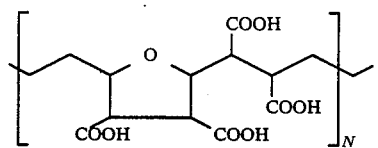

POLY(MALEIC ANHYDRIDE-CO-
DIVINYLETHER), (PYRAN)

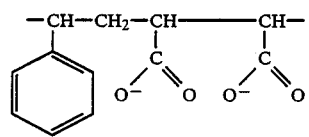

POLY(MALEIC ANHYDRIDE-CO-
STYRENE) (MA-ST)

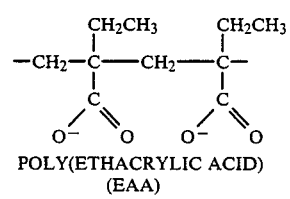

POLY(ETHACRYLIC ACID)
(EAA)

-continued

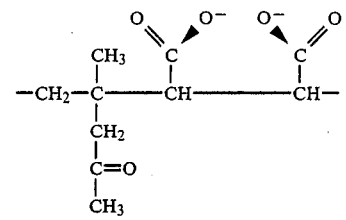

POLY(MALEIC ANHYDRIDE-
CO-4-METHYL-2-PENTANONE)

The polymer P ligand on the Pt(IV) complexes of this invention usually bears a water-solubilizing group which enhances the solubility in water of the platinum complexes of the invention, compared to the starting Ptamine complexes. Usually the polymer has a plurality of acidic functions which can be converted to their salt in alkaline solution, e.g., aqueous sodium bicarbonate. This renders the complex more readily soluble in water and facilitates its dissolution in a sterile injection vehicle for intravenous infusion. The water solubility of cisplatin is about 1 mg/ml in water. The platinum complexes of this invention having equivalent potency to cisplatin will advantageously have at least equivalent solubility.

It will be understood that significantly more potent antitumor agents can be administered in more dilute solutions and the requirement for water solubility is less critical. On the other hand, relatively high solubility in water can be most advantageous for antitumor agents, since it permits administration in a concentrated solution, i.e., in a small volume of injection or infusion vehicle. This can be particularly advantageous where it is desirable to administer the antitumor agent in the vicinity of a tumor location, e.g., by intravenous or intraarterial administration over a relatively short period of time for maximum impact at the tumor site. The more soluble complexes are also more readily assimilable when taken orally.

Preferably, the solubility of a complex according to the invention is at least about 1 mg/ml in water having a pH of 7 or higher, e.g., 1% NaHCO$_3$, more preferably at least about 10 mg/ml. For more potent complexes, a solubility of at least about 0.01 mg/ml is preferable, more preferably at least about 0.1 mg/ml in water or dilute alkali.

Useful and preferred types of water-solubilizing groups are phenolate, carboxylate, sulfonate or phosphonate groups, preferably sulfonate or carboxylate, which functional groups permit facile dissolution of the complex in dilute aqueous bicarbonate. Because of these acidic functions, the platinum complex of the invention may be provided as a pharmaceutically acceptable salt thereof, e.g., a sodium, potassium, magnesium, or calcium salt, or the like.

Preferred classes of platinum-polymer conjugates of this invention are complexes of polycarboxylic acids, e.g., those having one of the following formulae:

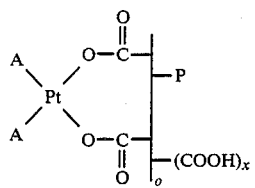

I(a)

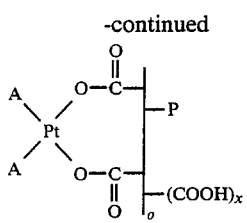

I(b)

or Pt(IV) complexes of one of the following general structures:

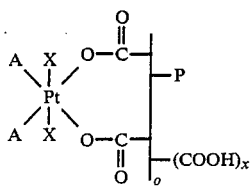

II(a)

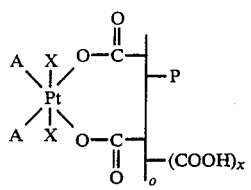

II(b)

In the above formulae, each A, which can be alike or different, is a m nodentate amine or $NH_3$; A A is a bidentate amine; ⊢P is the polymeric backbone of a biodegradable or a biostable but biocompatible polymer and "—(COOH)$_x$" represents any residual non-complexed pendant —COOH groups on the polymeric unit bearing the Pt-amine complex, e.g., x is 0 to 100, preferably 1 to 10; and o is a positive integer up to 500; and X is an anion; and salts thereof with bases.

Especially preferred Pt complexes of this invention wherein:

(a) Pt is Pt(II), i.e., those of Formula I, Ia and Ib;

(b) the amine ligand of the complex is a primary amine, especially those of (a), above;

(c) $A_2$ is a bidentate amine, especially those of (a) or (b), above;

(d) $A_2$ is DACH, especially trans-DACH, especially those of (a), above;

(e) the polymer is a partially or completely oxidized, water-soluble polysaccharide, at least two of whose primary hydroxy groups have been oxidized to carboxylic acid groups, especially those of (a), (b), (c) or (d), above;

(f) the polymer is a biodegradable polycarboxylic acid derivative of amylose, amylopectin, dextran, alginic acid or polygalacturonic acid;

(g) the polymer bears an average of from 50 to 2000, preferably 500 to 1700 carboxylic acid groups per polymer molecule, especially those of (a), (b), (c), (d), (e) or (f), above;

(h) the polymer is a polyacrylic or polymethacrylic acid, or copolymers especially those of (a), (b), (c), (d), (e) or (f), above;

(i) an average of from about 5 to about 500, preferably about 100 to 500, most preferably about 200 to 500 (about 100 to 200 for biodegradable polymers), Pt-amine moieties are complexed to each polymer molecule, especially those of (a), (b), (c), (d), (e), (f), (g) or (h), above.

In the Pt(IV) complexes of this invention, X can be any negatively charged inorganic or organic ion, e.g., hydroxy, halogen, e.g., Cl, Br or I, nitro, sulfato, phosphato, or an organic radical bearing a carboxylic or sulfonic acid group, e.g., a pendant carboxylic acid group of another monomeric unit or another molecule of the same polymer forming the complex with the Pt(IV) amine complex or of a different acidic polymer.

The polymers of Formulae I, Ia, Ib, IIa and IIb preferably contain up to about 1,000 repeating polymeric units, preferably about 250 to 800 for biodegradable polymers and about 50 to 400 for biostable polymers. Ordinarily up to about 500 platinum-amine complexes are present in each polymer molecule. Higher platinum contents are achieved by increasing the molar ratio of starting platinum amine complex to the starting acidic polymer or by the use of polymers having a readily accessible pendant carboxylic acid group on each polymer unit, e.g., polyacrylic acid. Lower platinum concentrations are achieved with lower molar ratios and with polymers having relatively few carboxylic acid groups per molecule or whose spacial configuration promotes cross-linking thereof by the platinum-amine complex rather than intramolecular linkages.

The polymer complexes of this invention are readily prepared from the corresponding $A_2Pt(II)X_2$ and $A_2Pt(IV)X_4$ platinum-amine complexes by simple mixing in a solvent in which both are soluble, usually water, preferably at a mildly acidic pH, e.g., 4–6.5. If X is a highly acidic ion, e.g., chloro or nitro, the pH is maintained in that pH range by the addition of a base, e.g., NaOH or $NaHCO_3$ as the platinum-amine complex complexes with the polymer. Usually a substantial molar excess, e.g., from about 1.5 to 3 fold excess, calculated on the starting platinum-amine complex, is employed. The reaction temperature is preferably maintained at about 0°–30°, more preferably about 5°–20° C.

The platinum-amine-polymer complex is ordinarily highly water soluble and therefore must be isolated by fractional precipitation or freeze drying. Excess starting polymer will ordinarily remain in solution if the reaction product solution is diluted with a water-soluble organic solvent, e.g., ethanol or isopropanol, until the polymer complex precipitates therefrom.

PREPARATION OF OXIDIZED POLYSACCHARIDES

The anhydropyranose units of the polysaccharides to be complexed were first oxidized with periodate to dialdehydes using a modified procedure of Claes et al., J. Virol. 313 (1970), then oxidized further to the dicarboxylic acid derivatives with chlorite from a procedure by Hofreiter et al., J. Am. Chem. Soc. 1, 6457 (1957), as follows:

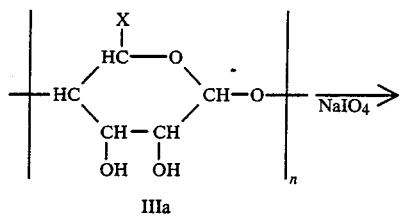

IIIa

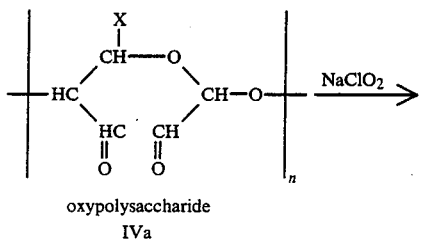

oxypolysaccharide
IVa

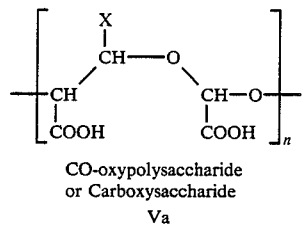

CO-oxypolysaccharide
or Carboxysaccharide
Va x = CH₂OH, carboxyamylose and carboxyamylopectin
(1-6 branched chain)
x = COOH, carboxyalginic acid and polygalacturonic acid.

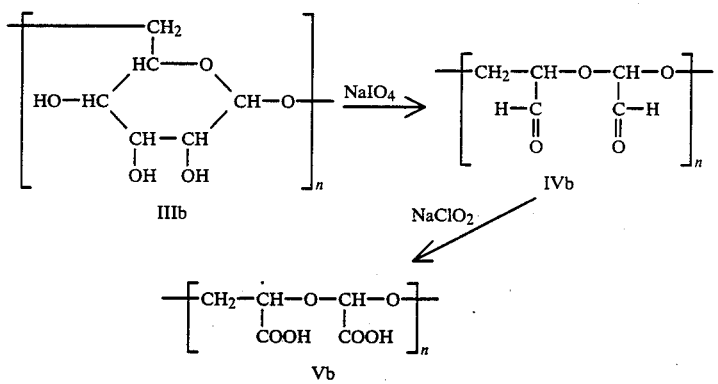

In the above formulae X is H or OH and n is an integer corresponding to the number of repeating polymeric units in the polymer.

COMPLEXING POLYACRYLIC AND POLYMETHACRYLIC ACIDS

Polyacrylic and Polymethacrylic Acids are believed to complex with Pt(trans-DACH) dinitrate according to the following reaction scheme:

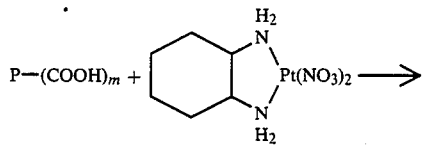

-continued

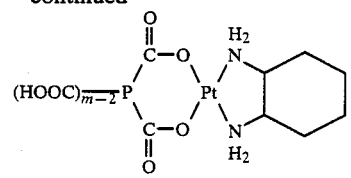

wherein P is the polymer backbone of the acid polymer, —COOH is the pendant carboxylic acid group, m is a large positive integer, for example, in the order of about 25 to 350, e.g., about 33, 83 or 250, in the case of the polyacrylic acids, and about 69 or 208, in the case of the polymethacrylic acids, and n is a positive integer corresponding to the number of Pt complexes in each molecule. It is believed that the Pt complexes are formed within each polymer molecule. However, it is possible that some of the complexes form cross-links with one or more other polymer molecules. To the extent any of these alternative structures are formed, they are within the scope of the novel complexes of this invention.

COMPLEXING CO-OXYPOLYSACCHARIDES TO PT(TRANS-DACH)DINITRATE:

The CO-oxypolysaccharides were complexed with Pt(trans-DACH)dinitrate in aqueous solution at room temperature at low pH according to the following reaction scheme:

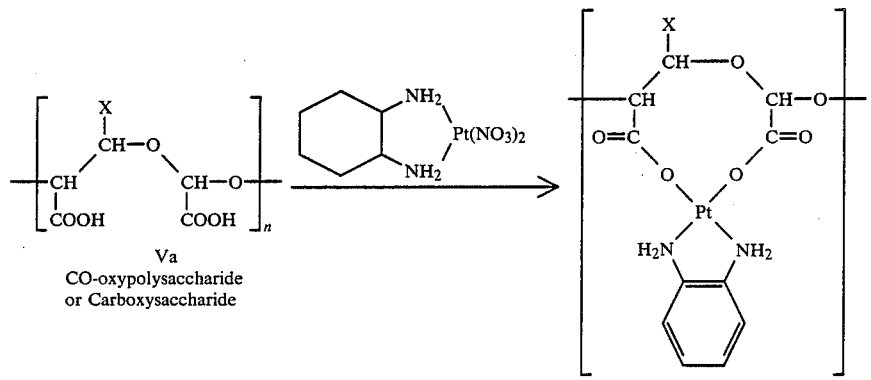

Va
CO-oxypolysaccharide
or Carboxysaccharide wherein $X=CH_2OH$ (amylose, amylopectin) or COOH (alginic and polygalacturonic acid), m is the number of polymer units per molecule and n is the average number of Pt complexes formed in the molecule.

The platinum complexes of this invention interfere with certain metabolic processes and are therefore useful as antitumor agents for the treatment of systemic and solid tumors which are responsive to platinum, e.g., cisplatin, therapy. They are also useful as antiviral, antiinflammatory and trypanocidal agents and are useful in the treatment of autoimmune disorders, such as AIDS, which render the affected person susceptible to a variety of opportunistic infections and to rarer cancers, e.g., Kaposi's Sarcoma.

The platinum complexes of the invention are advantageously administered to patients, i.e., humans or animals having a tumor susceptible to therapeutic treatment by platinum complexes, in admixture with a pharmaceutically acceptable carrier or diluent, in an antitumor-effective amount or concentration per unit dosage. The complexes are orally active and can be administered in any conventional liquid, semi-liquid or solid form, e.g., aqueous solutions or suspensions, elixirs, tablets, capsules, pills, which is adapted for oral administration. Depending on the stability, the potency, the bioavailability and the side effects of a particular compound, oral administration is preferred. However, as sterile aqueous solutions, they can be administered intravenously or intraarterially, and these other forms of administration may be indicated in certain cases.

Solutions for intravenous injections will normally be sterile physiological solutions, which may also contain appropriate amounts of alkali, e.g., sodium bicarbonate, to convert complexes bearing acidic water-solubilizing groups to their salts. It is also possible to use pharmaceutically acceptable surfactants, e.g., naturally occurring constituents of blood which have surface active properties, e.g., salts of bile acids such as deoxycholic acid, as dispersing and/or emulsifying agents. Such natural emulsifiers have been used to disperse antibiotics, e.g., amphotericin B, in aqueous injection media. Preferably, however, the water-solubilizing group(s) will render the platinum-polymer complex of the invention soluble in water without the use of such emulsifiers and/or surfactants. Suitable dosage forms can also include oily or aqueous injectable preparations, e.g., for intramuscular or intraperitoneal injection, syrups and the like liquid preparations, and solid dosage forms, e.g., capsules, tablets, dragees and the like.

The effective amounts of a complex of the invention which should be administered can be determined by conventional methods which will be apparent to the skilled clinician. Normally, the activity of a platinum complex of the invention will be evaluated in a screen along with a known complex such as cisplatin or the (DACH)Pt(II) complexes of Gale or Kidani. The relative potency and the therapeutic index, i.e., the ratio of therapeutic effectiveness to toxicity, compared to that of the known analogue will normally determine the relative dosage compared to conventional dosages of the analogue for the type of malignancy being treated. The treatment regimen can be varied in ways which are well known to the skilled clinician, as a function of the type of malignancy being treated, the condition of the patient, and the particular properties of the antitumor platinum complex being administered. Inevitably, a certain amount of experimentation is required to determine the optimum dosages and treatment regimens, as is normally the case for antitumor therapy. It will sometimes be advantageous to administer a platinum complex of the invention in combination with one or more agents that potentiate its antitumor activity or mitigate undesired side effects. Such synergistic effects have been disclosed in, e.g., Gale et al., U.S. Pat. No. 4,137,248, where a platinum complex was administered with cyclophosphamide and 5-fluorouracil or hydroxyurea.

An antitumor-effective dosage, e.g., an amount of a complex of the invention suitable for delivery of an equivalent amount of diaminoplatinum ions to the amount of such ions released by the complexes of Gale or Kidani, will generally be in the range of about 0.1–500 mg/kg/dose.

It is recognized that certain of the platinum-polymer complexes of this invention may have sufficiently high toxicity and/or sufficiently low therapeutic indices as to be unsuitable for antitumor therapy generally. However, these parameters can be readily determined by conventional screening tests, e.g., with L-1210 murine leukemia cells implanted in mice.

Without being bound by any mechanism or theory, it is nevertheless considered likely that the platinum-polymer complexes act as efficient drug delivery vehicles which deliver a higher percentage of the administered Pt ions to the tumor cells, thereby rendering smaller molar dosages thereof as antitumor effective as higher molar dosages of prior art Pt complexes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

PREPARATIONS

Preparation 1—Isotactic and Syndiotactic Poly(methyl methacrylate):

Isotactic poly(methyl methacrylate) was prepared by the method of Hatada et al., using a Grignard reagent as initiator. See Polym. J. 17:8, 977 (1985). t-Butyl magnesium bromide (5 m moles) was prepared by suspending magnesium (30 m moles) in anhydrous diethyl ether (12 ml) and adding t-butyl bromide (20 m moles) in diethyl ether (7 ml) slowly under argon with stirring and refluxing for 1 hour. When the reaction was complete, tbutyl magnesium bromide (0.2 moles) was mixed with anhydrous toluene (5 ml) under argon and the reaction vessel was cooled to $-78°$ C. Methyl methacrylate (10 m moles) was injected slowly into the initiator solution with a syringe and the reaction vessel was closed off under argon. The reaction was allowed to proceed for 48 hours before terminating with 2N HCl. The reaction time, temperature, and ratio of initiator to methyl methacrylate in this synthesis produces poly(methyl methacrylate) with a molecular weight of 5000 daltons. The polymer was precipitated out of the reaction solution with hexane, filtered, washed several times with hexane and dried under vacuum. The polymer was then dissolved in benzene, the benzene solution was filtered and the polymer was recovered by evaporating off the benzene under argon. Yield (100%).

Syndiotactic poly(methyl methacrylate) was prepared by the method of Bovey, J. Polym. Sci. Pt A, 1, 843 (1963), using potassium persulfate as initiator. A solution of potassium persulfate (125 mg) and sodium mercaptoacetate (25 mg) in water (10 ml) was stirred under argon until all persulfate was dissolved. Then methyl methacrylate (25 m moles) was added to the aqueous solution and the reaction mixture was heated for 3 hours at 50° C. at pH 2.0. The polymer was then precipitated with acetone and dried under vacuum. Yield (84%).

Preparation 2—Isotactic and Syndiotactic Poly(meth)acrylic acid:

Poly(methyl methacrylates) were hydrolyzed to poly(methacrylic acids) with concentrated sulphuric acid. See Seki et al, Macromolecules 17, 1692 (1984). Poly(methyl methacrylate) (1 g) was dissolved in conc. sulphuric acid (100 ml) and was stirred at room temperature for 10 days. The solution was poured into 50 g of ice and the precipitated polymers were filtered and redissolved in 1 N potassium hydroxide (100 ml) to cleave any anhydride rings that may form in sulphuric acid. The basic solution was heated for 3 hours at 80° C., then added to 0.5 N HCl to precipitate the polymers. The polymers were filtered and dried in a vacuum oven.

Preparation 3—Carboxysaccharides

To prepare a dialdehyde (IVa) (IVb), and 11% solution of sodium periodate was prepared and cooled in an ice-bath. Enough polysaccharide (IIIa),(IIIb) was added to make a final 3.0–3.6% solution, and the mixture was stirred in an ice-bath for 6 hours, then overnight at room temperature under protection from light. The dialdehydes with a molecular weight of 10,000 and over, with the exception of alginic acid and polygalacturonic acid, were insoluble in aqueous solution and could be easily filtered on Whatman filter paper #4 and then washed with water and ethanol. The smaller oxypolysaccharides, oxypolygalacturonic acid and alginic acid were water soluble and could be precipitated out of solution with two volumes of rapidly stirring ethanol, then filtered and washed with ethanol and acetone.

Use of an 11% solution of periodate ensures a degree of oxidation of 99%. A lesser degree of oxidation could be obtained by limiting the amount of periodate, as reported by Claes et al, J. Virol. 313 (1970). Reducing the percentage of periodate reduces the degree of oxidation by a corresponding percentage (i.e., reducing the theoretical amount of oxidizing agent by 50% gives a degree of oxidation of approximately 50%, etc.). The degree of oxidation was determined by reacting unused periodate in the filtrate with sodium arsenite and subsequently titrating unconsumed arsenate with an iodine solution.

The washed dialdehydes were then added to solutions of 1 M $NaClO_2$ in 0.5 M acetic acid to make a final concentration of 2% oxypolysaccharide. The mixture was stirred for 3 hours at room temperature in a fume hood and the sodium salts of the thus produced dicarboxylic acids (Va),(Vb) were precipitated out of solution by pouring the aqueous reaction mixture into two volumes of rapidly stirring ethanol. The CO-oxypolysaccharides were filtered with Whatman filter paper #4, and washed with small amounts of ethanol, then acetone, and dried overnight at room temperature in a vacuum oven.

Partially oxidized polysaccharides tended to precipitate out of ethanol/water solutions as gummy products. A granular form was obtained with these compounds by redissolving the filtered products in water and reprecipitating with two volumes of ethanol until a crystalline solid was obtained.

The dicarboxylic acids (Va),(Vb) were characterized by IR, which showed a peak at 1610 $cm^{-1}$ (Carboxylate ion assym. str.). The presence of carboxylic acid groups was also determined by the use of a detecting reagent for organic acids.

EXAMPLES

In the examples hereinafter, the platinum in every instance is Pt(II).

Preparation of (trans-DACH)Polyacrylate Complexes:

Three polyacrylic acid polymers of weight average molecular weight 2000, 5000, 15,000 were used as ligands for complexation with $Pt(DACH)(NO_3)_2$ to determine the effect of molecular weight on the physical properties and antitumor properties of the complexes. The ratio of polymer to platinum was increased to enhance the aqueous solubility of these complexes. In addition to polyacrylic acids, polymethacrylic acid of 15,000 weight average molecular weight and isotactic and syndiotactic polymethacrylic acid polymers of about 5000 $\overline{M}_w$ were used as ligands. The polyacrylates were complexed with Pt(DACH)(NO$_3$)$_2$ in aqueous solution at pH 4–6. The solubilities of these complexes are given in Table 1. The solubility of the thus-produced platinum-polymer complexes increases with a decrease in the molecular weight of the polymer, with an increase in polymer:Pt ratio, and by a work-up of the reaction mixture at low temperature.

TABLE I

Aqueous Solubilities of Polymeric Platinum Prodrugs

| DACH-Pt Polymer Complex | No. of Repeating Units of Polymer per Platinum Atom | NSC No. | Solubility (mg/ml) | Appearance |
|---|---|---|---|---|
| Carboxy Dextran 11,700 $M_w$ | 6 | 608912 | 100 | clear |
| Carboxy Dextran 11,700 $M_w$ | 2 | | 25 | cloudy |
| Carboxy Amylose 176,000 $M_w$ | 6 | 608913 | 10 | clear |
| Carboxy Amylopectin 176,000 $M_w$ | 6 | 608911 | 25 | clear |
| Carboxy Amylose 61,000 $M_w$ | 6 | | 20 | cloudy |
| Carboxy Dextran 47,000 $M_w$ | 3 | | 730 | clear |
| Carboxy Amylose 176,000 $M_w$ | 4 | 608916 | 725 | clear |
| Carboxy Amylopectin 176,000 $M_w$ | 4 | 608917 | 725 | clear |
| Poly(acrylic Acid) 5,000 $M_w$ | 5 | 608914 | 725 | clear |
| Alginic Acid | 4 | | 25 in 1% NaHCO$_3$ | clear |
| Polyglacturonic Acid | 4 | | 20 in 1% NaHCO$_3$ | clear |
| Poly(acrylic Acid) 15,000 $M_w$ | 4 | | >25 mg | clear |
| Poly(methacrylic Acid) 15,000 $M_w$ | 4 | 608352 | >25 mg | clear |

General Synthesis

Pt(trans-DACH)(NO$_3$)$_2$ was dissolved in a minimal amount of water with gentle heating and stirring until a clear solution was obtained. This was added to an aqueous solution of the polymer and the pH was adjusted between 4.5–6, depending upon the molecular weight of the polymer. The reaction was stirred for 12 hours at room temperature and the solid platinum-polymer complex was obtained by freeze-drying or by precipitation with ethanol. The complex was stirred and washed with a large excess of methanol and dried under vacuum.

EXAMPLE 1.

Pt(trans-DACH)polyacrylate (2000 $\overline{M}_w$)

Pt(trans-DACH)(NO$_3$)$_2$ (0.0005 moles) was dissolved in 5 ml of water. 2,000 $\overline{M}_w$ polyacrylic acid (0.00534 moles) was diluted with 5 ml of water and added to the Pt(DACH)(NO$_3$)$_2$ solution. The pH of the solution was adjusted to 5.5 with sodium hydroxide and the mixture was stirred at room temperature overnight. A small amount of the precipitate formed was removed by filtration and the filtrate was freeze-dried, washed thoroughly with methanol, and dried under vacuum to give 85% yield of the product. The infrared spectrum of the complex gave a peak at 1720 cm$^{-1}$ for the free carboxyl group and at 1620 cm$^{-1}$ for the platinum-bound carboxyl group. The disappearance of NO$_3$ stretch at 998 cm$^{-1}$ and 1370 cm$^{-1}$ indicated the completion of the reaction. The complex was very soluble in water.

EXAMPLE 2.

Pt(trans-DACH)Polyacrylate (5000 $\overline{M}_w$)

Pt(trans-DACH)(NO$_3$)$_2$ (0.0005 moles) was dissolved in 5 ml of deionized water by slight warming and stirring. 5,000 $\overline{M}_w$ polyacrylic acid (0.00411 mole) was diluted with 5 ml of water and filtered to remove suspended particles. The pH of the polymer solution was raised to 6.2 and Pt(trans-DACH)(NO$_3$)$_2$ solution was added dropwise while maintaining a pH of 6 by the addition of sodium hydroxide. No precipitate was observed. The reaction mixture was stirred overnight, freeze-dried, washed with excess methanol and dried under vacuum to give 85% of the product. Infrared spectrum of the title complex indicated the presence of bound and unbound carboxyl groups and the disappearance of the nitrate group. The title complex was very soluble in water.

EXAMPLE 3.

Pt(trans-DACH)Polyacrylate (15.000 $\overline{M}_w$)

Pt(trans-DACH)(NO$_3$)$_2$ (0.001 mole) was dissolved in 6 ml of deionized water by slight warming and stirring. 15,000 $\overline{M}_w$ polyacrylic acid (0.0082 mole) was diluted with 10 ml of water, the pH of the solution was raised to 6.4 and the platinum solution was added dropwise while maintaining a pH of 6. A small amount of white precipitate was formed. The precipitate was removed by filtration and the filtrate stirred overnight. The filtrate was freeze-dried, washed with methanol and dried under vacuum to give 70% yield of the title product. IR spectrum indicated complex formation.

EXAMPLE 4.

Pt(trans-DACH)Polymethacrylate (15.000 $\overline{M}_w$)

Pt(trans-DACH)(NO$_3$)$_2$ (0.005 moles) was dissolved in 5 ml of water by gentle heating and stirring. 15,000 $\overline{M}_w$ polymethacrylic acid (0.003 moles) was diluted with 5 ml of water and Pt(trans-DACH)(NO$_3$)$_2$ was added while maintaining a pH of 6. The solution was stirred overnight, freeze-dried, washed with excess methanol, and dried under reduced pressure to give a quantitative yield of the product. Infrared spectrum of the complex indicated the formation of the title platinum polymer complex.

Preparation of Pt(trans-DACH) Complexes with Isotactic and Syndiotactic Poly(methacrylic Acids)

These platinum complexes were prepared by a similar procedure as described above for the synthesis of Pt(DACH)polymethacrylate complex.

Pt(trans-DACH) Carboxy Polysaccharide Complexes

In addition to the synthesis of platinum complexes with polyacrylic acids and polymethacrylic acid, biodegradable polymers (carboxy polysaccharides) were also used to form complexes with (DACH)platinum. The following ligands were complexed with Pt(trans-DACH)(NO$_3$)$_2$: Carboxy amylose, carboxy amylopectin, carboxy dextrans whose weight average molecular weights were 10,000, 18,000 and 40,000; carboxy dextran sulfate of 5,000 weight average molecular weight, and oxidized polygalacturonic and alginic acid.

Preparation of (DACH)-Complexes with Oxidized Polysaccharides

Pt(trans-DACH)dinitrate was dissolved in a minimal amount of water with gentle heating and stirring until a clear solution is obtained. This solution was then added to a 7% solution of CO-oxypolysaccharide and the reaction pH was adjusted to 4.5 (nitric acid). The reaction was stirred for 4 hours at room temperature. Then the resultant Pt(DACH)carboxy polysaccharide complex was precipitated out of solution, e.g., by pouring the reaction mixture into two volumes of ethanol under rapid stirring. The larger (>10,000 $\overline{M}_w$) complexes precipitated out of solution immediately, whereas the smaller molecular weight complexes did not precipitate out well at room temperature (RT) and must be placed in an ice bath for several minutes before filtering to ensure complete precipitation. The precipitated product was filtered (Whatman filter paper) and washed extensively with a water-miscible organic solvent, e.g., acetone.

EXAMPLE 5.

Pt(trans-DACH)Carboxy Amylose (176.000 $\overline{M}_w$)

Amylose 150,000 $\overline{M}_w$ (3.6 g) was added to 145 ml of a solution of 11% sodium periodate and stirred in an ice bath for 6 hours, then overnight at room temperature under protection from light. Oxyamylose precipitated out of solution and was filtered and washed with 2×25 ml water and then with 50 ml ethanol. The compound tested positive with Schiffs reagent. All of the dialdehyde was added to 160 ml 1 M NaClO$_2$ in 0.5 M acetic acid and the mixture stirred for 3 hours at room temperature. The water soluble carboxy amylose was precipitated out of solution by pouring into 320 ml of rapidly stirring ethanol. The product was filtered and washed with 50 ml EtOH, then 100 ml acetone, and dried in a vacuum oven overnight at RT. White powder Yield=88%.

Pt(trans-DACH)(NO$_3$)$_2$ (0.0005 moles) was dissolved in 5 ml water. The thus-produced carboxy amylose (0.003 moles) was dissolved in 10 ml of water, mixed with the Pt(DACH)(NO$_3$)$_2$ and the reaction pH adjusted to 4.5. The reaction was allowed to proceed for 4 hours at room temperature and the title compound was isolated by freeze-drying to yield a pale yellow powder. Solubility at RT 10 mg/ml. Yield=58.5%.

EXAMPLE 6.

Pt(trans-DACH)Carboxy Amylose (4,800 $\overline{M}_w$)

Amylose 4,100 $\overline{M}_w$ (1 g) was poured into 50 ml of an 11% solution of NaIO$_4$ in an ice-bath and stirred at 4° C. for 6 hours, then at RT overnight under protection from light. Oxyamylose was precipitated out of solution with 100 ml EtOH under rapid stirring, then filtered and washed with 3×7.5 ml EtOH, then 50 ml MeOH, then with 3×25 ml acetone.

The thus-produced dialdehyde was poured into 220 ml 1 M NaClO$_2$ in 0.5 M acetic acid and stirred for 3 hours at RT. The mixture was poured into 440 ml of EtOH while stirring, whereby the CO-oxyamylose precipitated immediately out of solution. The product was filtered and washed with 3×50 ml acetone and dried overnight in a vacuum oven to yield white powder in 98.5% yield.

Pt(trans-DACH)(NO$_3$)$_2$ (0.0005 moles) was dissolved in 5 ml of H$_2$O and added to 0.003 moles of the thusproduced CO-oxyamylose (4,800). The reaction pH was adjusted to 4.5 and the reaction mixture stirred for 4 hours at RT. The product was precipitated out of solution with 30 ml EtOH, filtered and washed with 3×10 ml acetone to yield the title compound as a pale yellow powder. Solubility at 50° C.=20 mg/ml. Yield=37.5%.

EXAMPLE 7.

Pt(trans-DACH)Carboxy Amylopectin (176.000 $\overline{M}_w$)

Amylopectin 150,000 $\overline{M}_w$ (3.6 g) was added to 145 ml of a cold solution of 11% NaIO$_4$, stirred at 4° C. for 6 hours, then at RT overnight. Oxyamylopectin precipitated out of solution and was washed with 2×50 ml water, then 2×50 ml EtOH, and added to 280 ml of 1 M NaClO$_2$ in 0.5 M acetic acid. After stirring for 3 hours at RT, CO-oxyamylose was precipitated out of solution with 360 ml EtOH, filtered, washed with 3×50 ml acetone, and dried under vacuum overnight. White flaky powder. Yield=91.7%.

Pt(trans-DACH)dinitrate (0.0005 moles) was dissolved in 5 ml water and added to 0.0225 moles COoxyamylopectin in 10 ml water. The reaction pH was adjusted to pH 4.5 and the mixture stirred for 4 hours at RT. The product was freeze-dried. Pale yellow powder. Solubility at 50° C.=25 mg/ml. Yield=75.6%.

Pt(DACH)(NO$_3$)$_2$ (0.0005 moles) dissolved in 5 ml water was added to 0.003 moles of the thus-produced CO-oxyamylose, the pH adjusted to 4.5 and the mixture stirred 4 hours at RT. The complex was precipitated out of solution with 30 ml EtOH and washed with 3×10 ml acetone to yield the title compound as a pale yellow powder. Solubility at 50° C.=25 mg/ml. Yield=82%.

EXAMPLE 8.

Pt(trans-DACH)Carboxy Dextran (11.700 $\overline{M}_w$)

Dextran 10,000 $\overline{M}_w$ (3 g) was added to 145 ml of a cold 11% solution of $NaIO_4$, stirred for 6 hours at 4° C., then overnight at RT. The dialdehyde was water soluble and was precipitated out of solution with 300 ml EtOH washed with 3×50 ml EtOH and added to 180 ml 1 M $NaClO_2$ in 0.5 M acetic acid and stirred for 3 hours at RT. The CO-oxydextran solution was poured into 400 ml EtOH. The precipitated product was filtered and washed with 3×50 ml acetone to yield a fluffy white powder. Yield=91%.

Pt(trans-DACH) $(NO_3)_2$ (0.0005 moles) in 5 ml of water was added to 0.001 moles of the thus-produced carboxy dextran $M_w$ 10,000 in 10 ml of water, the pH adjusted to 4.5 and the mixture stirred for 4 hours at RT. The complex was precipitated out of solution with 30 ml EtOH and washed with 3×10 ml acetone. Yellow powder. Solubility at 50° C.=25 mg/ml. Yield=76.7%.

The title complex with a Pt:CO-oxydextran molar ratio of 1:6 was prepared by the General Synthesis method described above and isolated as a pale yellow powder. Solubility at RT 100 mg/ml. Yield=66%.

EXAMPLE 9.

Pt(trans-DACH)Carboxy Dextran (21,200 $\overline{M}_w$)

Dextran $\overline{M}_w$ 18,000, 3 g was added to 145 ml of a cold 11% solution of $NaIO_4$, stirred for 6 hours at 4° C., then overnight at RT. The dialdehyde was precipitated out of solution with 400 ml EtOH and washed with 2×50 ml EtOH, and added to 170 ml of 1 M $NaClO_2$ in 0.5 M acetic acid and stirred at RT for 3 hours. The CO-oxydextran was precipitated out of solution with 400 ml EtOH and washed with 3×50 ml acetone. Light yellow powder. Solubility at room temperature: 100 mg/ml. Yield=61%.

EXAMPLE 10.

Pt(trans-DACH)Carboxy Dextran (47,000 $\overline{M}_w$)

Dextran 40,000 $\overline{M}_w$ (3 g) was added to 145 ml of a cold solution of 11% $NaIO_4$, stirred at 4° C. for 6 hours, then overnight at room temperature. The dialdehyde was water insoluble and was filtered, washed with water and ethanol and suspended in 250 ml of 1 M $NaClO_2$ in 0.5 M acetic acid and stirred for 3 hours at room temperature. CO-oxydextran was precipitated out of solution with 500 ml EtOH and washed with 3×50 ml ethanol.

The thus-produced CO-oxydextran (0.0003 moles) was dissolve din 10 ml water and to this was added a solution of 0.0005 moles of Pt(DACH)dinitrate in 5 ml $H_2O$ and the reaction pH adjusted to 4.5. The product precipitated out of solution during the reaction time of 4 hours, while stirring at room temperature, to yield the title compound as a yellow precipitate. The product was insoluble in water at room temperature and up to 50° C. Yield=60%.

EXAMPLE 11.

Pt(trans-DACH)Carboxy Dextran Sulfate (6,000 $\overline{M}_w$)

Dextran sulfate 5,000 $\overline{M}_w$ (3 g) was dissolved in 145 ml of 11% $NaIO_4$ and stirred for 6 hours at 4° C., then overnight at room temperature. A small amount of precipitate was present, which was filtered off and discarded. The oxydextran sulfate was precipitated out of solution with 300 ml ethanol and washed with 50 ml ethanol, then 2×50 ml acetone.

The gummy product was added to 160 ml of 1 M NaCl in 0.5 M acetic acid and the mixture stirred for 3 hours at room temperature. The carboxylic acid was precipitated out of solution by pouring into 400 ml of rapidly stirring ethanol and placing in an ice bath for several minutes. The product was washed with 5 ml ethanol and then with 2×100 ml acetone. After washing with acetone, it still retained its gummy character and was dried in a vacuum oven overnight at 37° C. to obtain a granule form thereof.

Pt(trans-DACH)dinitrate (0.0005 moles) in 5 ml $H_2O$ was added to 0.003 moles of the thus-produced CO-oxydextran sulfate in 10 ml $H_2O$ and the reaction pH adjusted to 4.5. The mixture was stirred overnight at room temperature and the title compound was precipitated out of solution with 30 ml acetone and washed with 40 ml EtOH, then 50 ml acetone to yield a yellow powder. Solubility at RT 50 mg/ml. Yield=28%.

EXAMPLE 12.

Pt(trans-DACH)Carboxy Dextran, 11,700 $\overline{M}_w$ (58% Degree of Oxidation)

Dextran 10,000 $\overline{M}_w$ (3 g) was added to 290 ml of a 5% solution of $NaIO_4$ and stirred for 6 hours at 4° C., then overnight at room temperature. The oxydextran did not precipitate out of solution. 600 ml of EtOH was added under rapid stirring to precipitate the dialdehyde. The oxydextran was washed with 100 ml acetone and added to 160 ml of 1 M $NaClO_2$ in 0.5 M acetic acid and stirred at room temperature for 3 hours. The dicarboxylic acid was precipitated out of solution with 350 ml EtOH and washed with 3×50 ml acetone Titration of CO-oxydextran showed a degree of oxidation of 58%.

The thus-produced 58% oxidized carboxy dextran was complexed with Pt(DACH)dinitrate in a ratio of Pt:Polymer of 1:6. Pt(DACH)dinitrate (0.0005 moles) in 5 ml $H_2O$ was added to 0.003 moles of the thus-produced CO-oxydextran in 10 ml $H_2O$ and the reaction pH adjusted to 4.3. The reaction mixture was stirred overnight at RT. The solution was then poured into 50 ml ethanol. A small amount of white precipitate formed, which was filtered off. The filtrate was placed in an ice-bath, whereby the title compound appeared as a yellow precipitate (the white precipitate contained no Pt). The yellow product was washed with 2×50 ml acetone. Solubility =100 mg/ml at room temperature. Yield=28%.

EXAMPLE 13.

Pt(trans-DACH)Carboxy Amylose (50% degree of Oxidation)

Amylose (3 g) was added to 290 ml of a solution of 5% $NaIO_4$, stirred at 4° C. for 6 hours, then overnight at room temperature. The precipitated dialdehyde was filtered and suspended in 160 ml of 1 M $NaClO_2$ in 0.5 acetic acid and stirred for 3 hours at room temperature. The partially-oxidized carboxy amylose was precipitated out of solution with 320 ml EtOH at 4° C. The gummy product had to be redissolved in $H_2O$ and re-precipitated with 2 volumes of ethanol 4 times before a granular form was obtained. The product was dried in a vacuum oven overnight at room temperature. Final yield of CO-oxyamylose was 37%.

The thus-produced CO-oxyamylose (0.0003 moles) was dissolved in 10 ml $H_2O$ and added to 0.0005 moles Pt(DACH)dinitrate and the reaction pH adjusted to 4.5. The mixture was stirred for 4 hours at room temperature to produce the title compound which was obtained as a white powder. Solubility at 50° C.=25 mg/ml. Yield=71.6%.

EXAMPLE 14.

Pt(trans-DACH)Carboxy Polygalacturonic Acid

Polygalacturonic acid (3.6 g) was added to 145 ml of an 11% solution, stirred at 4° C. for 6 hours, then overnight at room temperature. The dialdehyde did not precipitate out of solution. The reaction mixture was poured into 2 volumes ethanol and oxypolygalacturonic acid was filtered and washed with 2×50 ml ethanol, then added to 160 ml 1 M $NaClO_2$ in 0.5 M acetic acid and stirred for 3 hours at room temperature. The solution was poured into 2 volumes (320 ml) rapidly stirring ethanol, filtered and washed with 2×50 ml ethanol then 2×50 ml acetone.

The thus-produced CO-oxypolygalacturonic acid (0.003 moles) in 10 ml of $H_2O$ was mixed with 0.0005 moles Pt(DACH)dinitrate in 5 ml $H_2O$, the reaction pH adjusted to 4.5 and the mixture stirred for 4 hours at room temperature, whereby a precipitate of the title compound formed during the reaction, which was isolated as a white powder. Insoluble in aqueous solution. Yield=46%.

EXAMPLE 15.

Pt(trans-DACH)CO oxyalginic Acid (75.000 $\overline{M}_w$)

Alginic acid (3.6 g) was added to 145 ml 11% sodium periodate, stirred at 4° C. for 6 hours, then at room temperature overnight. The dialdehyde was soluble in water and was precipitated out of solution with 150 ml EtOH. The degree of oxidation was found to be 80.5%. The dialdehyde was added to 160 ml 1 M $NaClO_2$ in 0.5 M acetic acid, the mixture stirred at room temperature for 3 hours and the CO-oxyalginic acid precipitated out of solution with two volumes of ethanol. The product was washed with 2×100 ml EtOH, then 2×100 ml acetone. The yield of CO-oxyalginic acid was 99%.

The thus-produced CO-oxyalginic acid (0.003 moles) was dissolved in 10 ml water. To this was added 0.0005 moles Pt(DACH)(NO$_3$)$_2$ in 5 ml water and the reaction pH adjusted to 6.0. The mixture was stirred overnight and the thus-produced Pt(DACH)CO-oxyalginic acid was precipitated out of solution with 30 ml of ethanol, washed with 2×50 ml ethanol and then 3×50 ml acetone. Yield=89.3%. Solubility in 10% sodium bicarbonate solution=25 mg/ml at 40° C.

Preparation of Pt(trans-DACH)Carboxy Polysaccharide Complexes by Freeze-Drying

EXAMPLE 16.

Pt(trans-DACH)Carboxyamylose (176,000 $\overline{M}_w$)

Pt(trans-DACH)(NO$_3$)$_2$ (0.0005 moles) was dissolved in 5 ml of water by gentle stirring and warming. Carboxy amylose (0.00245 moles) was dissolved in 10 ml of water and filtered to remove any suspended particles. The two solutions were mixed and the pH of the mixture was adjusted to 5.28. The reaction mixture was stirred at room temperature overnight, lyophilized, and was washed with methanol, and dried under vacuum to give a quantitative yield of the product. The solubility of the complex was greater than 25 mg per ml on slight warming.

EXAMPLE 17.

Pt(trans DACH)Carboxy amylopectin (176,000 $\overline{M}_w$)

Carboxy amylopectin (0.00245 moles) was dissolved in 10 ml of water and filtered. Pt(trans-DACH)(NO$_3$)$_2$ (0.0005 moles) was dissolved in 5 ml of water and was added to the carboxy amylopectin solution. pH of the mixture was adjusted to 4.78 with nitric acid. The mixture was stirred overnight, lyophilized, washed with methanol, and dried under vacuum to give a quantitative yield of the product. The solubility of the complex was greater than 25 mg per ml.

EXAMPLE 18.

Pt(trans-DACH)Carboxy Dextran (40,000 $\overline{M}_w$)

Carboxy dextran (0.0018 moles) was dissolved in 10 ml of water. The pH of the solution was 5.7 and it was raised to 7 by the addition of sodium hydroxide. Pt(trans-DACH)(NO$_3$)$_2$ (0.0005 moles) was dissolved in 5 ml of water and added this solution dropwise to a solution of carboxy dextran while maintaining a pH of 6. A small amount of precipitate was formed. The reaction mixture was stirred at room temperature overnight, filtered, lyophilized and washed with methanol to give 90% of the product. The solubility of the complex was greater than 30 mg per ml.

Some of the specific compounds of the examples above were tested by NCI against L1210 murine tumor model in BDF$_1$ mice. The tumored mice were injected ip with solutions of compounds on days 1, 5, and 9 after the cell innoculum. The results of the experiments were evaluated on day 30 and are expressed as the quotient of the median survival time in days of test animals divided by median day of death of the untreated control mice, multiplied by 100 (T/C%). Mice with no sign of tumor on day 30 are considered as cured. The results of these experiments are given in Table 2.

TABLE 2

Activity of Pt(trans-DACH)Polymer Complexes vs. L1210 Mouse Leukemia

| Polymer | Repeating Units per Pt atom | Dose mg/kg | T/C (%) | Cures |
|---|---|---|---|---|
| Carboxyamylose ($\overline{M}_w$ = 176,000) | 4.5 | 10 | 337 | 5/6 |
| | | 20 | 337 | 3/6 |
| Carboxyamylose ($\overline{M}_w$ = 176,000) | 6 | 10 | 269 | 1/6 |
| | | 20 | 269 | 2/6 |
| | | 40 | 292 | 2/6 |
| Carboxyamylopectin ($\overline{M}_w$ = 176,000) | 4 | 10 | 357 | 3/6 |
| | | 20 | 261 | 1/6 |
| Carboxyamylopectin ($\overline{M}_w$ = 176,000) | 6 | 10 | 337 | 4/6 |
| | | 20 | 314 | 2/6 |
| Poly(acrylic acid) ($\overline{M}_w$ = 5,000) | 4 | 320 | 232 | 1/6 |
| Poly(methacrylic acid) ($\overline{M}_w$ = 15,000) | 4 | 80 | 224 | 1/6 |
| | | 140 | 202 | 1/6 |

T/C = Ratio of test evaluation to control evaluation expressed as percentage. More precisely, T/C = Median survival time of test animals × 100 (Median survival time of control).

Antitumor activity of some of these compounds against L1210 is compared in Table 3.

TABLE 3

Comparison of Platinum Content, Dosage, and Activity of Some of the Novel Complexes against Cisplatin in L1210 Tumor Line

| Compound | % Pt | Dose (mg/kg) | T/C | Cures |
|---|---|---|---|---|
| Cisplatin | 65 | 5 | 175 ± 5 | — |
| Pt(trans-DACH) | 10 | 10 | 337 | 5/6 |
| Carboxyamylose | | 20 | 337 | 3/6 |
| Pt(trans 10.2 | 10 | 337 | 4/6 | |
| Carboxyamylopectin | | 20 | 314 | 2/6 |

In addition to the L1210 tumor line, Pt(trans-DACH-)carboxyamylose (Pt:Polymer=1:6) was screened against additional murine tumor models. In these experiments, tumor of a known weight was implanted subcutaneously to the mice. The mice were then treated with the compound on day 1, 5, 9 schedule. On day 30, the tumors were reweighed and the results are expressed as percent inhibition of tumor weight. The screening data is given in Table 4.

TABLE 4

Antitumor Activity of Pt(trans-DACH)Carboxyamylose Against Solid Tumors

| Tumor | Dose | % Inh. |
|---|---|---|
| x5563 Plasma | 5 | 100 |
| Cell Myeloma | 10 | 100 |
| | 20 | 100 |
| M5 ovarian | 5 | 64 |
| Carcinoma | 10 | 86 |
| | 20 | 99 |
| Lewis Lung | 1.25 | 20 |
| | 2.5 | 37 |
| | 5 | 34 |
| CA - 755 | 5 | 69 |
| Adenocarcinoma | 10 | 81 |
| | 20 | 94 |

EXAMPLE 19.

(trans-DACH) Pyran Copolymer Complex

Pyran copolymer (MVE-2; Hercules Inc.) as received from the manufacture (92 mg) was dissolved in water (3 ml) by dropwise addition of 2 N sodium hydroxide. Final pH of the solution was 12. It was stirred at this pH for 25 minutes for complete conversion of pyran to carboxylate groups and was added to the solution of Pt(trans-DACH) (NO$_3$)$_2$ (100 mg) in 2 ml of water. The pH of the reaction mixture was adjusted to 4.93 by the dropwise addition of 2 N nitric acid. It was stirred at room temperature for two hours and was desalted by passing through a small column packed with Sephadex G-25. The complex was precipitated by the addition of 10 ml of ethanol. Yield was 90%. Infrared spectrum of the complex indicated the presence of free and platinum-bound carboxyl groups.

This complex exhibits anti-tumor activity against tumors responsive to cisplatin and/or DACH-Pt and bisplatinum complex therapy.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A polymeric platinum-amine complex of the formula

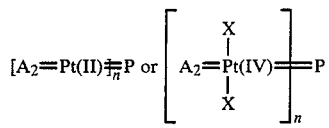

wherein
each A independently represents a monodentate amine ligand or NH$_3$ or A$_2$ represents a single bidentate amine ligand;
n is a positive integer up to 500;
P is a divalent ligand of a physiologically acceptable homopolymer or copolymer bearing at least 2×n pendant anionic groups, pairs of which form covalent linkages with the Pt(II)A$_2$ or Pt(IV)A$_2$ group; and
X is an anionic ligand.

2. A platinum complex according to claim 1, wherein the platinum is Pt(II).

3. A platinum complex according to claim 1, wherein A$_2$ is the bidentate 1,2-diaminocyclohexane ligand.

4. A platinum complex according to claim 1, wherein n is about 100 to 500.

5. A platinum complex according to claim 1, wherein the physiologically acceptable polymer is a biostable polymer having a weight average molecular weight of about 10,000 to 50,000 or a biodegradable polymer having a weight average molecular weight of about 5,000 to about 200,000 and containing only C, H and O atoms.

6. A platinum complex according to claim 1, wherein the physiologically acceptable polymer is a biodegradable polycarboxylic acid derivative of amylose, amylopectin, dextran, alginic acid or polygalacturonic acid.

7. A platinum complex according to claim 1, wherein the physiologically acceptable polymer is complexed with 1,2-diaminocyclohexane platinum.

8. A platinum complex according to claim 7, wherein the platinum is Pt(II).

9. A platinum complex according to claim 8, wherein the physiologically acceptable polymer is a biostable polymer having a weight average molecular weight of about 10,000 to 50,000 or a biodegradable polymer having a weight average molecular weight of about 5,000 to about 200,000 and containing only C, H and O atoms and wherein n is about 100 to 500.

10. A Pt(trans-DACH)carboxy amylose platinum complex according to claim 1.

11. A Pt(trans-DACH)carboxyamylopectin platinum complex according to claim 1.

12. A Pt(trans-DACH)carboxydextran platinum complex according to claim 1.

13. A Pt(trans-DACH)Co-oxyalginic acid platinum complex according to claim 1.

14. A Pt(trans-DACH)carboxy polygalacturonic acid platinum complex according to claim 1.

15. A Pt(trans-DACH)pyran copolymer platinum complex according to claim 1.

16. A platinum complex according to claim 1, wherein the physiologically acceptable polymer is a biostable polymer having a weight average molecular weight of about 10,000 to 50,000 or a biodegradable polymer having a weight average molecular weight of about 5,000 to about 200,000 and containing only C, H, and O atoms, and wherein the physiologically acceptable polymer is a biodegradable polycarboxylic acid derivative or amylose, amylopectin, dextran, alginic acid, or polygalacturonic acid.

17. A method of treating a patient with a tumor susceptible to platinum therapy by administering thereto a platinum-amine complex which exhibits anti-tumor activity against L1210 tumors and solid tumors, which comprises administering the platinum-amine complex to the affected host as a conjugate with a water-soluble, physiologically acceptable anionic polymer, thereby reducing the amount of the complex required to be administered thereto to manifest the anti-tumor activity thereof in the patient.

18. In a method of treating a patient with a tumor susceptible to platinum therapy by administering thereto an antitumor-effective amount of a platinum complex the improvement wherein the complex is a platinum complex according to claim 1.

19. In a method of treating a patient with a tumor susceptible to platinum therapy by administering thereto an antitumor-effective amount of a platinum complex the improvement wherein the complex is a platinum complex according to claim 8.

20. In a method of treating a patient with a tumor susceptible to platinum therapy by administering thereto an antitumor-effective amount of a platinum complex the improvement wherein the complex is a platinum complex according to claim 9.

21. In a method of treating a patient with a tumor susceptible to platinum therapy by administering thereto an antitumor-effective amount of a platinum complex the improvement wherein the complex is a platinum complex according to claim 10.

22. In a method of treating a patient with a tumor susceptible to platinum therapy by administering thereto an antitumor-effective amount of a platinum complex the improvement wherein the complex is a platinum complex according to claim 11.

23. In a method of treating a patient with a tumor susceptible to platinum therapy by administering thereto an antitumor-effective amount of a platinum complex the improvement wherein the complex is a platinum complex according to claim 12.

24. In a method of treating a patient with a tumor susceptible to platinum therapy by administering thereto an antitumor-effective amount of a platinum complex the improvement wherein the complex is a platinum complex according to claim 13.

25. In a method of treating a patient with a tumor susceptible to platinum therapy by administering thereto an antitumor-effective amount of a platinum complex the improvement wherein the complex is a platinum complex according to claim 14.

26. A method of increasing the percentage of Pt ions of a diaminocyclohexane platinum (II) moiety which are delivered to the tumor cells of a tumor susceptible to platinum (II) therapy in a mammal, which method comprises administering to the mammal an amount effective to deliver an antitumor effective amount of said moiety to said tumor of a platinum complex according to claim 8.

* * * * *

UNITED STATES PATENT AND TRADEMARK OFFICE
CERTIFICATE OF CORRECTION

PATENT NO. : 4,931,553

DATED : June 5, 1990

INVENTOR(S) : DEVINDER S. GILL ET AL

It is certified that error appears in the above-identified patent and that said Letters Patent is hereby corrected as shown below:

Title page, field [73], Assignee:

should read as follows " Andrulis Research Corporation,
7315 Wisconsin Avenue,
Bethesda, Maryland 20814"

Signed and Sealed this

Twenty-fifth Day of June, 1991

Attest:

HARRY F. MANBECK, JR.

*Attesting Officer*

*Commissioner of Patents and Trademarks*